United States Patent [19]
Stewart

[11] Patent Number: 5,669,077
[45] Date of Patent: Sep. 23, 1997

[54] APPAREL WITH ONBOARD GROWTH CHART

[76] Inventor: Franklin L. Stewart, 1329 SW. 14th St., Apt. 308, Portland, Oreg. 97201

[21] Appl. No.: 652,161

[22] Filed: May 23, 1996

[51] Int. Cl.⁶ .................................................. A41D 1/06
[52] U.S. Cl. ............................ 2/227; 2/269; D2/742
[58] Field of Search ............................ 2/227, 269, 232, 2/123, DIG. 2, 75, 80, 243.1; D2/742, 744, 745, 746, 747

[56] References Cited

U.S. PATENT DOCUMENTS

| | | | |
|---|---|---|---|
| D. 164,706 | 10/1951 | Murphy | D2/742 |
| D. 259,145 | 5/1981 | Inoue | D2/747 |
| 259,931 | 6/1882 | Simmons | 2/DIG. 2 |
| 277,744 | 5/1883 | Kimball | 2/DIG. 2 |
| 1,520,832 | 12/1924 | McConnell | 2/123 |
| 2,360,953 | 10/1944 | Lippmann | 2/232 |
| 2,417,529 | 3/1947 | Terry | 2/227 |
| 2,985,887 | 5/1961 | Lindley . | |
| 3,168,749 | 2/1965 | Cala . | |
| 3,234,564 | 2/1966 | Chujfi | 2/227 |
| 3,601,817 | 8/1971 | Abrams et al. | 2/227 |
| 4,149,275 | 4/1979 | Sanchez | 2/227 |
| 4,200,938 | 5/1980 | LeTourneau | 2/269 |
| 4,683,595 | 8/1987 | Cash | 2/105 |
| 4,791,685 | 12/1988 | Maibauer | 2/227 |
| 5,006,393 | 4/1991 | Isoe . | |
| 5,204,995 | 4/1993 | Knapp | 2/227 |

FOREIGN PATENT DOCUMENTS

| | | | |
|---|---|---|---|
| 1564917 | 4/1969 | France | 2/227 |

OTHER PUBLICATIONS

Bates Motorcycle Asscessories Catalog, 1967–68, "Leather Pants for Men", p. 7.

*Primary Examiner*—Amy B. Vanatta
*Attorney, Agent, or Firm*—Kolisch, Hartwell, Dickinson, McCormack & Heuser

[57] ABSTRACT

A garment is provided with a first series of markings extending along its exterior and a second series of markings extending along its interior, the first and second series of markings being configured such that cuffing of the garment results in a predetermined portion of the second series of markings facing exteriorly to provide a selectively adjustable continuation of the first series of markings. The markings typically are in the form of characters of predetermined size, and are at intervals which accommodate cuffing of the garment to folds corresponding to predetermined units of measure. Relative growth of a wearer thus may be determined by identifying changes in relationship between the first and second series of markings over time.

19 Claims, 1 Drawing Sheet

APPAREL WITH ONBOARD GROWTH CHART

TECHNICAL FIELD

The present invention relates generally to apparel, and more particularly to apparel which includes an onboard chart for use in determining growth of a wearer over time. Although the concept has broad utility, it has proven especially well-suited for use in connection with children's trousers, and is described accordingly herein.

BACKGROUND OF THE INVENTION

For many years now, it has been common for parents to periodically mark their child's height on a wall in order to keep a record of the child's growth over time. This arrangement has proven unsatisfactory, however, due in part to the unsightly nature of such markings, and due to the increasingly mobile society in which we live. It will be understood, for example, that it is not possible to bring a marked wall along when visiting distant relatives or friends. It also may be difficult to preserve the markings when painting the wall or moving to a new home. Additionally, the act of placing marks on a wall typically will not allow distant relatives or friends to participate. What is needed is a growth chart which is not tied to a stationary structure such as a wall.

It therefore would be desirable to provide a system whereby a child's growth may be recorded for posterity without marring a wall or tying the record unnecessarily to a stationary object. It also would be desirable to incorporate such a system into a product which is useful whether or not it is desired to record a child's growth. Finally, it would be desirable to provide a growth chart which is fun to use, attractive to the eye, and suitable as a gift.

SUMMARY OF THE INVENTION

The aforementioned objectives are addressed by provision of a garment which includes a first series of markings extending along its exterior and a second series of markings extending along its interior, the first and second series of markings being configured such that cuffing of the garment results in a predetermined portion of the second series of markings facing exteriorly to provide a selectively adjustable continuation of the first series of markings. The markings typically are in the form of characters of predetermined size, and are at intervals which accommodate cuffing of the garment to folds corresponding to predetermined units of measure. Relative growth of a wearer thus may be determined by identifying changes in relationship between the first and second series of markings over time.

In the preferred embodiment, the interior characters are inverted relative to the exterior characters so as to provide for alignment of the all exteriorly-facing characters (including both interior and exterior characters) upon cuffing of the garment. Additionally, the exterior characters may define a repeating sequence of characters, the interior characters defining a corresponding repeating sequence of characters wherein the exteriorly-facing character on an outermost fold of a cuff follows in character sequence to a last character of the first series of characters. These characters also may be provided with regions configured to receive data in order to record information such as the date, the name and/or the age of the wearer. The characters may, in fact, take the form of selectively attachable/detachable pieces which are adhered to and removed from the garment as desired.

These and other objects and advantages which are achieved or offered by the present invention will become more fully apparent as the description which follows is read in conjunction with the accompanying drawings.

DETAILED DESCRIPTION OF THE PREFERRED EMBODIMENT AND BEST MODE OF CARRYING OUT THE INVENTION

Figure 1:
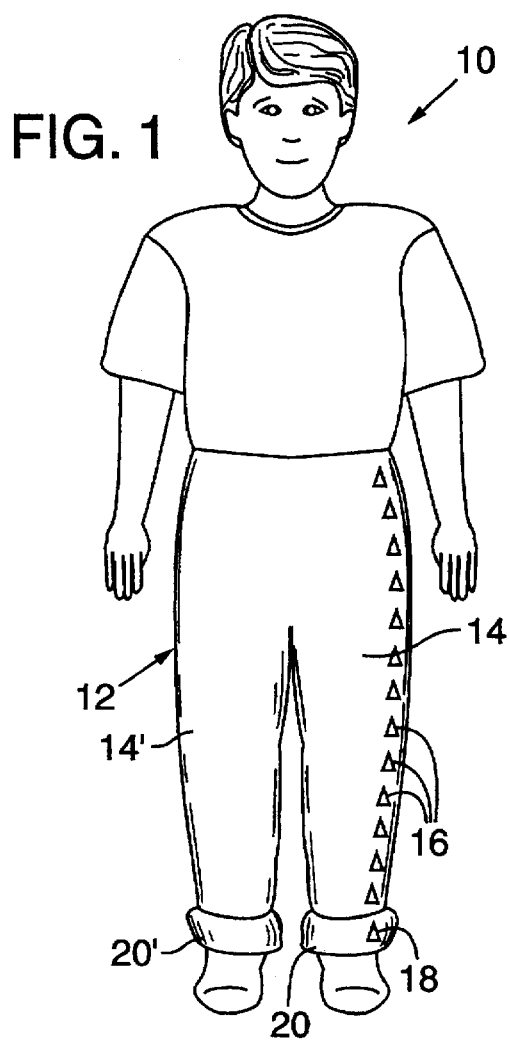
FIG. 1 is a front elevational view of an individual wearing trousers constructed in accordance with a preferred embodiment of the invention, such trousers including a series of markings along a right leg of the trousers.

Referring initially to FIG. 1, an individual 10 is shown wearing trousers 12, such trousers embodying the invented apparel with onboard growth chart. As indicated, the trousers include a pair trouser legs 14, 14', at least one of which carries a series of regularly spaced, exterior markings 16. That trouser leg also carries a series of regularly spaced interior markings 18, one of such markings being shown in FIG. 1 as facing exteriorly on a cuff of the trouser leg.

As indicated, the exterior markings typically extend along the entire length of the trouser leg, defining predetermined units of measure which aid in measuring the wearer's height. It will be understood, however, that the exterior markings may extend only along a somewhat shorter growth region defined near the bottom of the trouser leg so as to provide for measurement of the wearer's growth over time. The interior markings similarly may extend along the entire length of the trouser leg, but need only extend along the growth region as described above. Further, although the exterior and interior markings are shown on only one of the trouser legs, such markings may be provided on one or both of the trouser legs, and in various longitudinal portions thereof. Most typically, however, the markings will be applied in opposing fashion and will extend longitudinally along the side of the trouser leg.

In accordance with my teachings, it will be understood that the trouser legs may be cuffed (as shown at 20, 20') to fit the trousers to the wearer's size, each cuff being defined by one or more folds of material. As the wearer grows, the trouser leg may be uncuffed, thus increasing the effective length of the trouser leg and revealing previously-hidden folds. By revealing these folds, previously-hidden exterior and interior markings also are revealed, providing for selectively adjustable continuation of the markings which extend along the trouser leg. Also, interior markings which once were visible (i.e., markings which faced exteriorly on the cuff) are turned inwardly so as to hide such markings from view.

Figure 2:
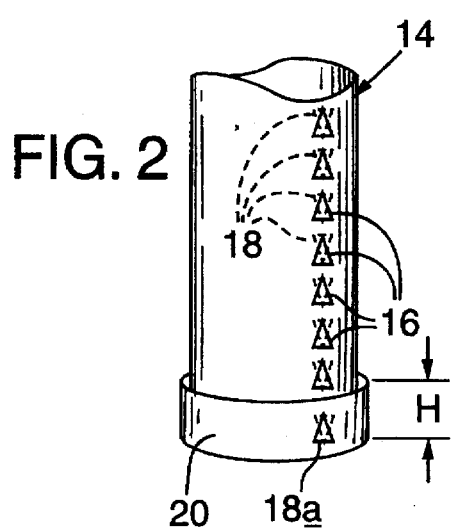
FIG. 2 is an enlarged front elevational view of the right leg of the trousers of FIG. 1, such leg including coincident interior and exterior markings which provide an adjustable growth indication system.

Turning now to FIG. 2, it will be seen that trouser leg 14 includes substantially similar interior markings (shown in dashed lines) and exterior markings (shown in solid lines) which typically are an integral part of the material from which the trousers are made. It will be understood, however, that such markings may be applied to an existing garment using patches, buttons, snaps, dye, paint, or any other mechanism whereby markings may be selectively adhered to the trouser leg. It may, in fact, be desirable to provide for selected removal of the markings to provide for variations in the garment appearance.

In the preferred embodiment, the markings define characters of predetermined height H, and thereby define predetermined units of measure. Accordingly, the trouser legs are cuffed to define folds of material which correspond to the predetermined character height, each fold defining a unit of measure whereby the relative growth of the wearer may be determined by comparing cuffing of a trouser leg from time to time. More particularly, it is possible to measure the relative growth of a wearer by identifying changes in relationship between the interior markings (e.g., the interior marking which appears on the cuff) and the exterior markings over time.

In order to provide for accurate measurement of the wearer, the interior and exterior markings are positioned directly opposite one another, defining corresponding interior and exterior measurement marks. Typically, both the interior and exterior markings are uniformly spaced, but the interior markings may be offset slightly so as to compensate for variations due to cuffing of the trouser legs. Such variations, however, may be avoided by selecting a relatively thin material for the trousers, or by ensuring that the cuffs are neatly creased.

For simplicity, the characters in FIG. 2 are shown uniformly as triangles, but those skilled will understand that virtually any type of character (e.g. alphanumeric characters, cartoon characters, etc.) could be employed. Where non-symmetrical characters are used, interior characters may be configured differently than exterior characters in order to provide for similar alignment of all exteriorly-facing characters when the trouser leg is cuffed. It will be appreciated, for example, that the exterior markings 16 are configured in a first predetermined orientation, and the interior markings 18 are configured in a second predetermined orientation inverted relative to the first predetermined orientation. Exteriorly-facing triangle 18a (on cuff 20) thus will be understood to be an interior marking which has been inverted by cuffing of the trouser leg. Accordingly, triangle 18a is placed in an orientation which conforms with the orientation of exterior markings 16.

Figure 3:
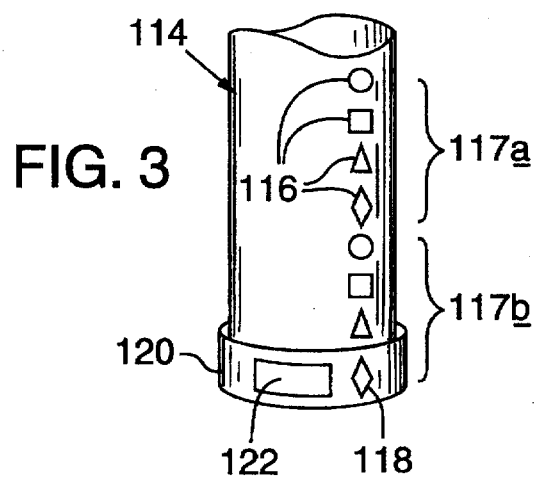
FIG. 3 is a front elevational view of an alternative trouser leg, such leg including a repeating sequence of exterior characters and a corresponding repeating sequence of interior characters configured to provide a selectively adjustable extension of the repeating sequence of exterior characters when the leg is cuffed.

FIG. 3 shows a trouser leg 114 which employs another embodiment of the invention, the trouser leg including markings which define a repeating sequence of characters 117a, 117b. A first series of markings 116 define the repeating sequence of characters on the exterior of the trouser leg, and a second series of markings 118 define the repeating sequence of characters on the interior of the trouser leg. As indicated, the interior and exterior markings are arranged such that the exterior-facing character (an interior marking 118) on the outermost fold of cuff 120 follows in character sequence to a next-adjacent marking of the exterior character sequence, thus maintaining the character sequence as the trouser leg is cuffed and uncuffed. This is accomplished by off-setting the interior character sequence relative to the exterior character sequence by one character (shown in FIGS. 3A and 3B).

Figure 3A:
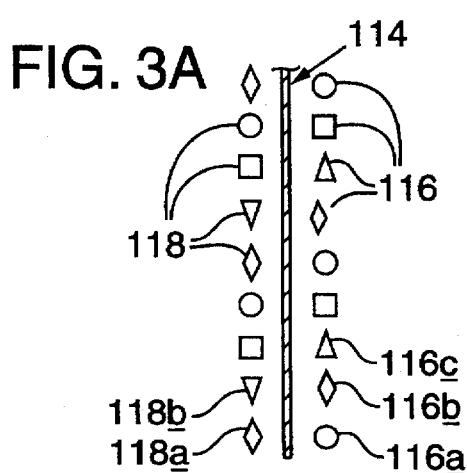
FIGS. 3A and 3B are somewhat schematic cross-sectional views demonstrating cuffing of a trouser leg similar to that depicted in FIG. 3, the interior and exterior characters of the leg being shown in areas adjacent to the surfaces on which such characters appear.
Figure 3B:
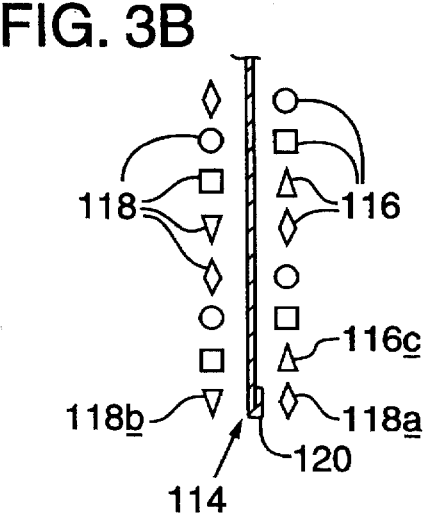

A cross section of trouser leg 114 is shown in somewhat schematic form in FIGS. 3A and 3B, the interior and exterior characters of the trouser leg being illustrated generally in areas adjacent to those portions of the trouser leg on which they would appear. As indicated in FIG. 3A, the uncuffed trouser leg includes a series of interior markings 118 with a lowermost character 118a, and a series of exterior markings with characters 116a, 116b and 116c. Upon folding the trouser leg to define a cuff as shown in FIG. 3B, characters 116a and 116b are covered by the cuff, and character 118a is made to face exteriorly. The last visible character in the exterior series of marking thus becomes character 116c. The lowermost character on the interior of the trouser leg becomes character 118b.

Looking again to FIG. 3, it will be noted that such figure also shows, at 122, a message region which is configured to receive data such as the date, age, name of the wearer, etc. In the preferred embodiment, the message region takes the form of a panel on which information may be written, but it is to be understood that various recording media may be used without departing from the concept set forth herein. Further, although a separate panel is shown in the depicted embodiment, the characters themselves may serve as message regions where information may be recorded for posterity.

Although the depicted apparel takes the form of trousers, those skilled in the art will recognize that the invented growth indication system may be employed in connection with a variety of apparel items, including shirts, skirts, jumpsuits, shorts, etc. Further, it will be understood that various size characters may be employed, and in various regions of the apparel to indicate various areas of growth.

Accordingly, while the present invention has been shown and described with reference to the foregoing operational principles and embodiments, it will be apparent to those skilled in the art that variations and changes in form and detail may be made therein without departing from the spirit and scope of the invention as defined in the appended claims.

I claim:

1. A growth indication system for use on a garment with an interior and an exterior, the system comprising:

a first series of markings formed along the exterior of the garment at regularly spaced intervals and in a first predetermined orientation; and a second series of markings formed along the interior of the garment at regularly spaced intervals and in a second predetermined orientation which is inverted relative to the first predetermined orientation;

said first and second series of markings being configured such that when the garment is cuffed, the second series aligns with the first series and a predetermined portion of the second series of markings face exteriorly to provide a selectively adjustable continuation of the first series of markings.

2. The system of claim 1, wherein the markings are configured to define predetermined units of measure.

3. The system of claim 2, wherein the first and second series of markings are configured to provide for measurement of relative growth of a wearer by identifying changes in relationship between the first and second series of markings upon progressive cuffing and uncuffing of the garment.

4. The system of claim 1, wherein the markings define characters of predetermined height.

5. The system of claim 4, wherein the cuffed garment defines one or more folds, each fold defining a length of material which corresponds to the predetermined character height.

6. The system of claim 5, wherein the markings define a repeating sequence of characters.

7. The system of claim 6, wherein the exteriorly-facing character on an outermost fold of the cuff follows in character sequence to a last character of the first series of markings.

8. The system of claim 1, wherein each marking defines a region configured to receive data.

9. The system of claim 1, wherein the markings are selectively adhered to the garment.

10. Trousers having a pair of legs, at least one of the legs including a growth indication system, the growth indication system comprising:

a first series of discrete characters of predetermined size extending vertically along an exterior of a predetermined leg at regularly spaced intervals; and a second series of discrete characters of predetermined size extending vertically along an interior of the predetermined leg at regularly spaced intervals;

said first and second series of characters being configured such that when the predetermined leg is cuffed, a predetermined portion of the second series of characters faces exteriorly in vertical alignment with the first series of characters to provide a selectively adjustable continuation of the first series of characters and to thereby define predetermined units for measuring growth of a wearer.

11. The trousers of claim 10, wherein the first and second series of characters are configured to provide for measurement of relative growth of an individual by identifying changes in relationship between the first and second series of characters upon progressive cuffing and uncuffing of the trouser leg.

12. The trousers of claim 10, wherein the cuffed trouser leg includes one or more folds, each fold defining a length of material which corresponds to the predetermined character size.

13. The trousers of claim 12, wherein the first series of characters define a sequence, the predetermined portion of the second series of characters following in character sequence to a last character of the first series of characters.

14. The trousers of claim 10, wherein the first series of characters are configured in a first predetermined orientation, and the second series of characters are configured in a second predetermined orientation which is inverted relative to the first predetermined orientation, whereby exteriorly-facing characters of the second series of characters align with characters of the first series of characters when the trouser leg is cuffed.

15. The trousers of claim 10, wherein the characters are selectively adhered to the trousers.

16. The trousers of claim 10, wherein each character defines a region configured to receive data.

17. Apparel with onboard growth indication system, the apparel having a selectively cuffed appendage with an interior and an exterior, the system comprising:

a first series of characters of selected height formed along the exterior of an appendage leg to define a predetermined sequence of characters at regularly spaced intervals and in a fast predetermined orientation; and a second series of characters formed along the interior of the appendage opposite the first series of characters in the predetermined sequence at regularly spaced intervals, the second series of characters being arranged in a second predetermined orientation inverted relative to the first predetermined orientation;

said first and second series of markings being configured such that when the appendage is cuffed, a predetermined portion of the second series of characters becomes inverted and faces exteriorly to provide a selectively adjustable continuation of the first series of characters in the predetermined sequence whereby measurement of relative growth of an individual may be made by identifying changes in relationship between the first and second series of characters upon progressive cuffing and uncuffing of the appendage.

18. The apparel of claim 17, wherein each character defines a region configured to receive data.

19. The apparel of claim 17, wherein the characters are selectively adhered to the appendage.

* * * * *